United States Patent [19]

Shoesmith

[11] Patent Number: Plant 5,280

[45] Date of Patent: Sep. 11, 1984

[54] CHRYSANTHEMUM PLANT NAMED MOONSTONE

[75] Inventor: Leonard H. Shoesmith, Surrey, England

[73] Assignee: Pan American Plant Company, Parrish, Fla.

[21] Appl. No.: 452,333

[22] Filed: Dec. 22, 1982

[51] Int. Cl.[3] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Moonstone particularly characterized by its semi-incurved globe shaped capitulum form and formal capitulum type, creamy yellow-white ray floret color, 10–14 cm. diameter across the face of the capitulum, uniform 9 week height with no long days, and its semi-upright branching habit.

2 Drawing Figures

The present invention comprises a new and distinct cultivar of *Chrysanthemum morifolium,* Ramat., hereinafter referred to by the cultivar name Moonstone.

Moonstone is a product of a planned breeding program which had the objective of creating new chrysanthemum cultivars with a semi-incurved globe shaped capitulum, creamy yellow-white ray florets, nine week flowering response, and the ability to produce commercially acceptable quality in year round cut mum programs. Such traits in combination were not present in previously available commercial cultivars.

Moonstone was originated from a hybridization made in a controlled breeding program in Westfield, Woking, England in 1976. The male and female parents are unknown at this time. Moonstone was discovered and selected as one flowering plant within the progeny of the stated parentage by Leonard H. Shoesmith on November, 1977 in a controlled environment in West Chicago, Ill. and given the code name 57-501-W.

The first act of asexual reproduction of Moonstone was accomplished when vegetative cuttings were taken from the initial selection on February, 1978 in a controlled environment in West Chicago, Ill. by a technician working under formulations established and supervised by Leonard H. Shoesmith. Horticultural examination of selected units initiated March, 1978 has demonstrated that the combination of characteristics as herein disclosed for Moonstone are firmly fixed and are retained through successive generations of asexual reproduction.

Moonstone has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Moonstone, which in combination distinguish this chrysanthemum as a new and distinct cultivar:

1. Semi-incurved globe shaped capitulum form.
2. Formal capitulum type.
3. Creamy yellow-white ray floret color.
4. Diameter across the face of the capitulum 10–14 cm.

5. Uniform 9 week photoperiodic flowering response to short days.
6. Height 1–1.5 m with no long days.
7. Semi-upright branching habit.

Of the many commercial cultivars known to the present inventor, the most similar in comparison to Moonstone is Bounty, a commercial standard disclosed in U.S. Plant Pat. No. 4,468, granted Oct. 23, 1979. In comparison to Bounty, Moonstone has creamy yellow-white flowers and is slightly less incurved. It is also 2–3 days earlier than Bounty and has a better stem. The vigor and formal capitulum type are similar to those same characteristics of Bounty.

The accompanying photographic drawings show typical inflorescence and foliage characteristics of Moonstone, with colors being as nearly true as possible with illustrations of this type. Sheet 1 is a color photograph in perspective of Moonstone. Sheet 2 is a black and white reproduction of typical foliage of Moonstone, shown abaxially.

In the following description color references are made to The Royal Horticultural Society Colour Chart. The color values were determined between 2:00–2:30 P.M. on Dec. 9, 1982 under 5000 foot candle natural light at Parris, Fla.

CLASSIFICATION

Botanical: *Chrysanthemum morifolium,* Ramat., cv Moonstone.

Commercial: Standard cut.

INFLORESCENCE

Capitulum:

*Form.*—Semi-incurved globe.

*Type.*—Formal.

*Diameter across face.*—10–14 cm.

Corolla of ray florets:

*Color (general tonality from a distance of three meters).*—Creamy yellow-white.

*Color (abaxial).*—158C.

*Color (adaxial).*—158C.

Corolla of disc florets:

*Color (mature).*—Yellow.

*Color (immature).*—Yellow/green.

Reproductive organs:

*Androecium.*—Present in disc florets only.

*Gynoecium.*—Present in both disc and ray florets

PLANT

General appearance:

*Height.*—1–1.5 m. given no long days year round.

Foliage:

*Color (abaxial).*—147B.

*Color (adaxial).*—147A.

*Shape.*—Deeply lobed and slightly serrated.

I claim:

1. A new and distinct chrysanthemum cultivar named Moonstone, as shown and described, and particularly characterized by its semi-incurved globe shaped capitulum form and formal capitulum type, creamy yellow-white ray floret color, 10–14 cm. diameter across the face of the capitulum, uniform 9 week photoperiodic flowering response to short days, 1–1.5 m height with no long days, and its semi-upright branching habit.

* * * * *

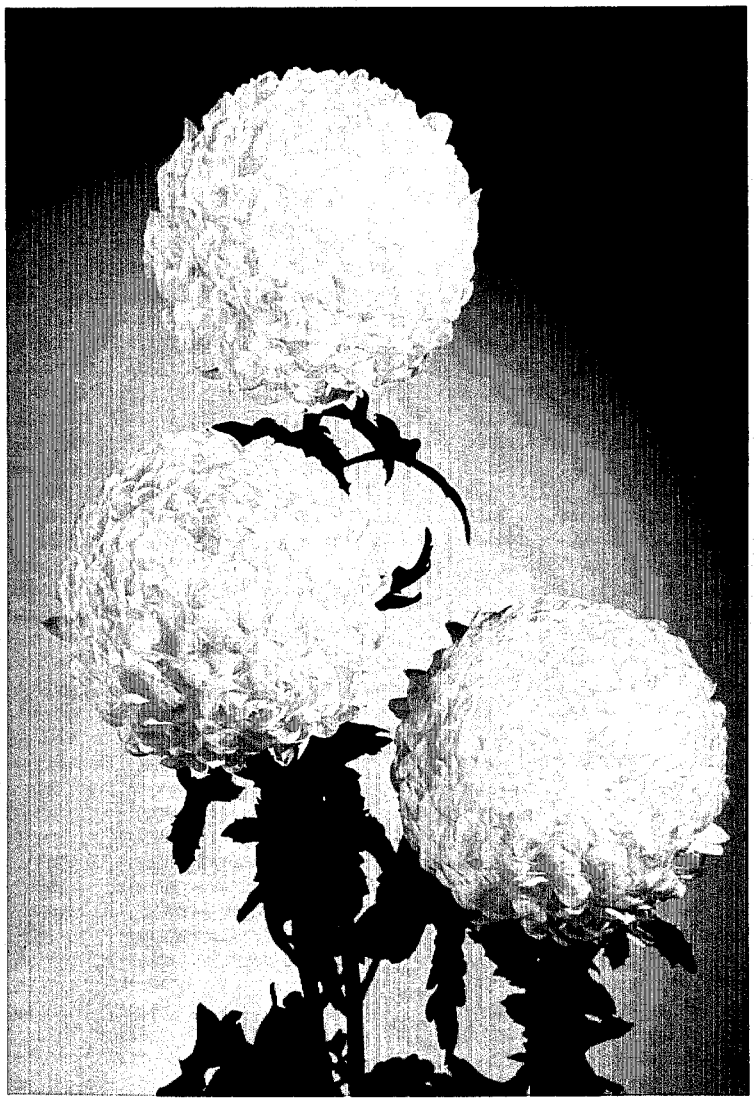

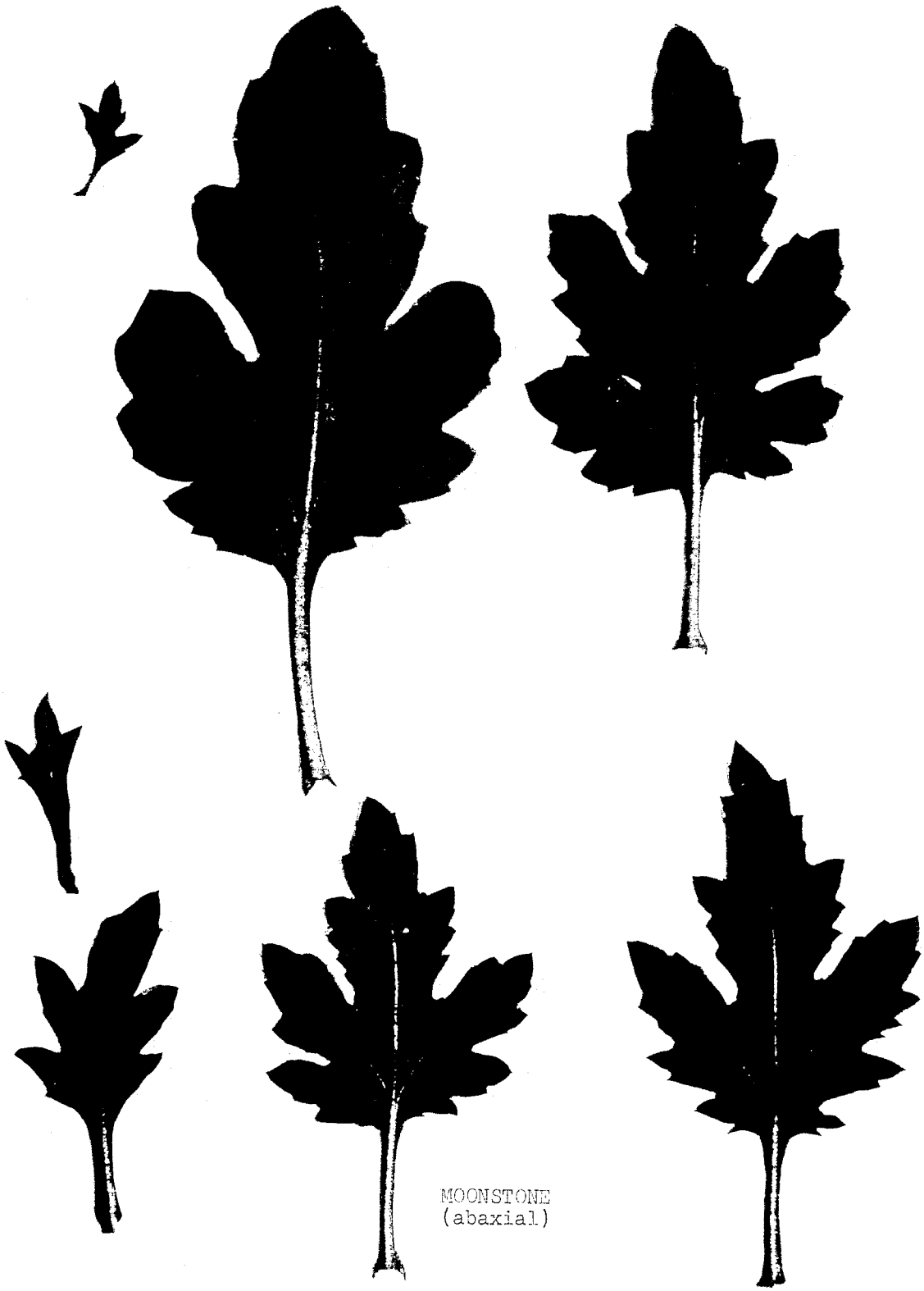
MOONSTONE
(abaxial)